United States Patent [19]
Spencer et al.

[11] Patent Number: 5,127,916
[45] Date of Patent: Jul. 7, 1992

[54] LOCALIZATION NEEDLE ASSEMBLY

[75] Inventors: Stephen F. Spencer; Thomas J. Jansen, both of Gainesville, Fla.

[73] Assignee: Medical Device Technologies, Inc., Gainesville, Fla.

[21] Appl. No.: 644,027

[22] Filed: Jan. 22, 1991

[51] Int. Cl.$^5$ .............................................. A61B 17/34
[52] U.S. Cl. ...................................... 606/185; 606/205
[58] Field of Search ............... 606/185, 205, 221; 604/116; 43/43.16, 34, 44.2

[56] References Cited

U.S. PATENT DOCUMENTS

| | | | |
|---|---|---|---|
| 620,896 | 3/1899 | Edgar | 43/43.16 |
| 627,179 | 6/1899 | Dreese | 43/43.16 |
| 779,843 | 1/1905 | Fredricks | 43/43.16 |
| 2,220,559 | 11/1940 | Voigt | 43/34 |
| 2,233,863 | 3/1941 | Driscoll | 43/43.16 |
| 2,266,725 | 12/1941 | Andrews | 43/43.16 |
| 2,541,246 | 2/1951 | Held | 606/205 |
| 2,645,054 | 7/1953 | Taylor | 43/44.2 |
| 3,397,477 | 8/1968 | Hand | 43/34 |
| 3,399,482 | 9/1968 | Cox | 43/34 |
| 3,624,950 | 12/1971 | Merckes | 43/44.2 |
| 4,592,356 | 6/1986 | Gutierrez | 606/185 |
| 4,774,948 | 10/1988 | Markham | 606/185 |
| 4,931,059 | 6/1990 | Markham | 606/185 |

Primary Examiner—Paul J. Hirsch
Attorney, Agent, or Firm—Emrich & Dithmar

[57] ABSTRACT

A localization needle assembly includes an outer tubular cannula and a reinforced needle structure slidably mounted for movement within the outer cannula between extended and retracted portions, the needle structure includes a rearwardly extending retractable barb and a non-retractable barb which are contained within the outer cannula when the inner needle structure is extended while the surgeon locates a lesion. When the target area is reached, the inner needle structure is retracted, and the retractable barb is deployed through an opening in the sidewall of the outer cannula for anchoring the localization needle assembly in body tissue in the proximity of the lesion. When positioning is satisfied with precise targeting of the lesion, the outer cannula is removed, leaving both the fixed and retractable barbs in place with both barbs deployed and localizing the lesion to be removed for biopsy procedure.

17 Claims, 6 Drawing Sheets

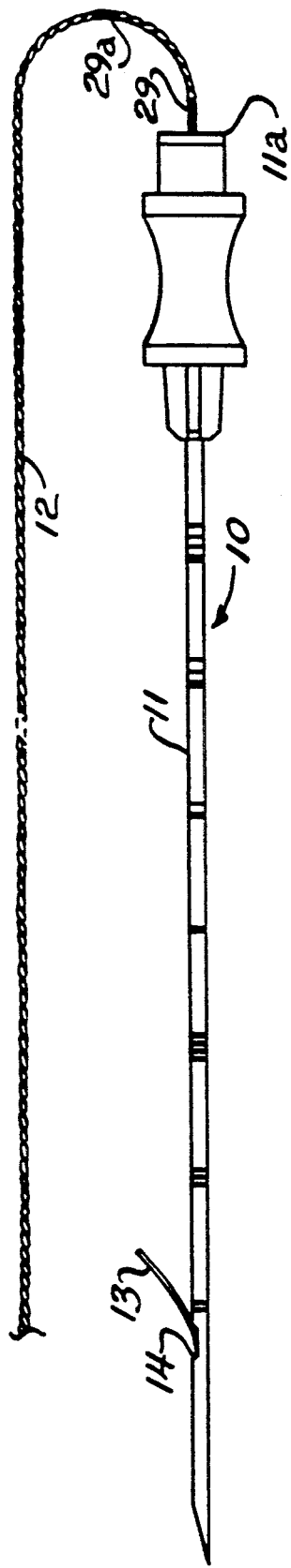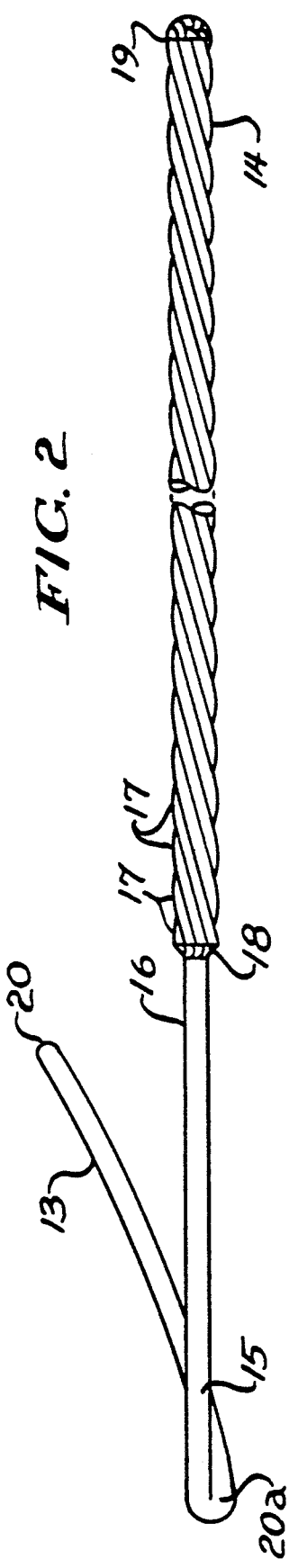

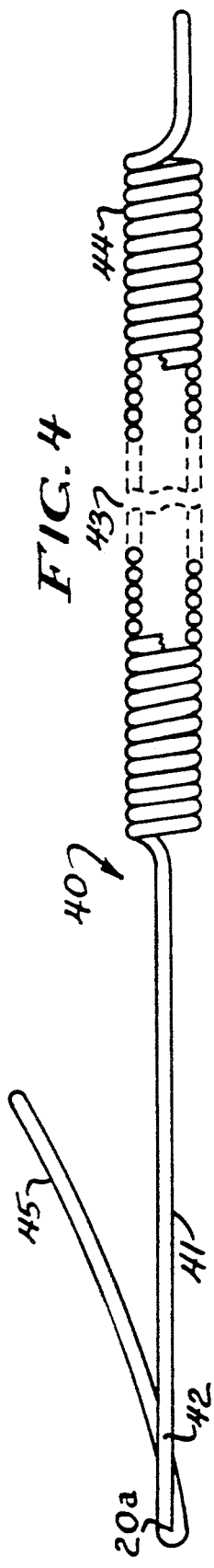
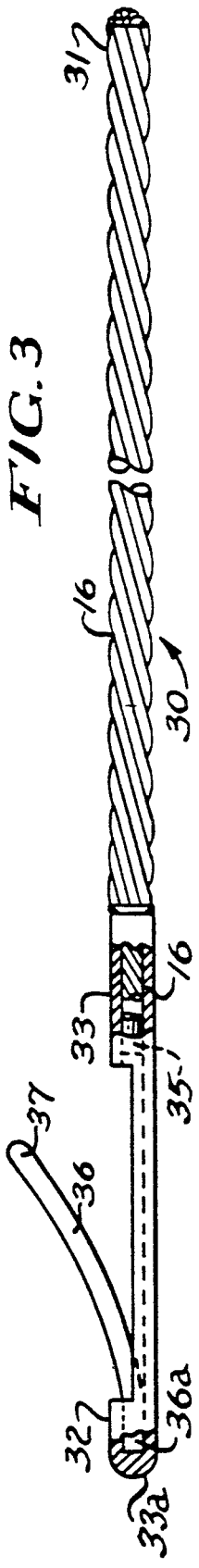
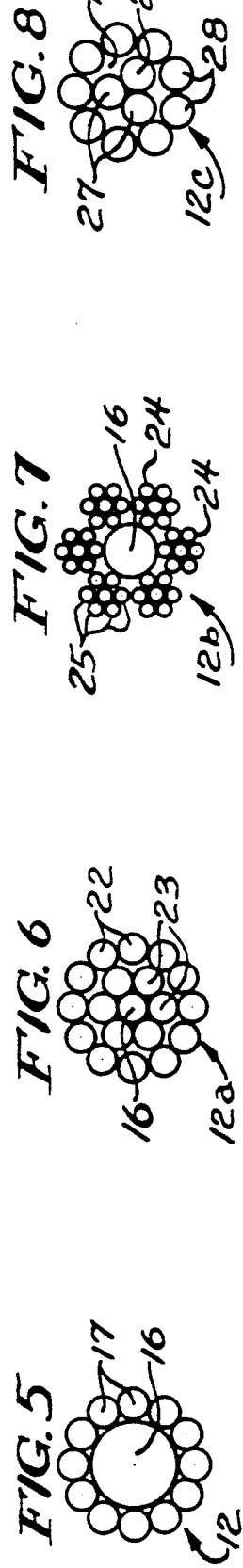
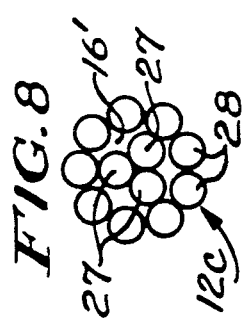
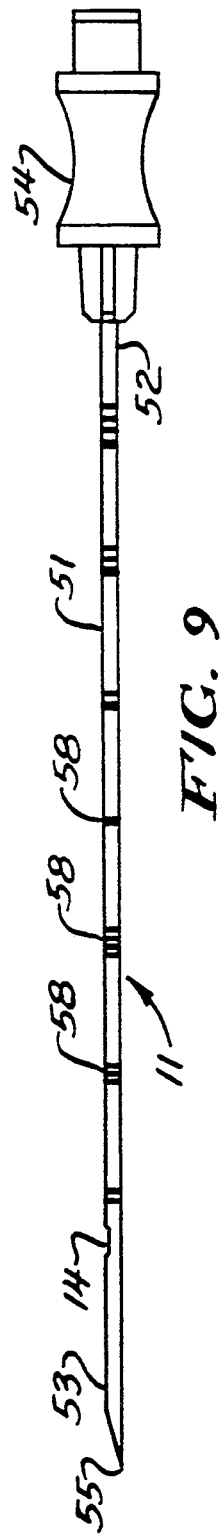

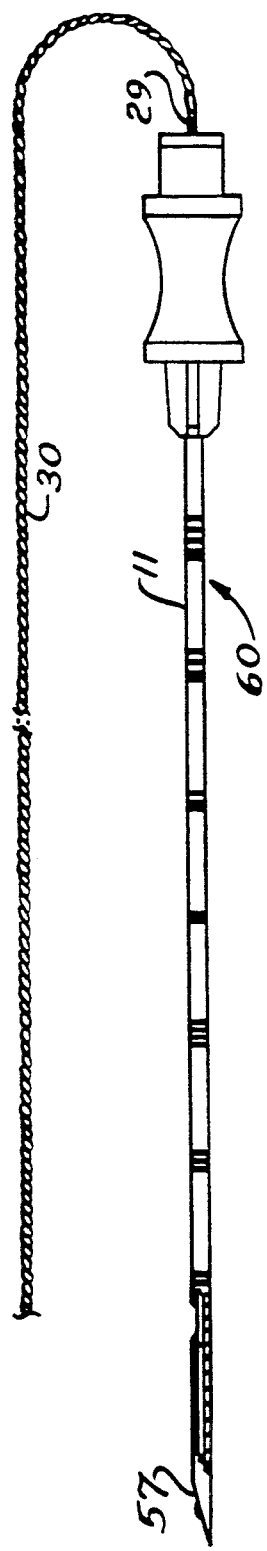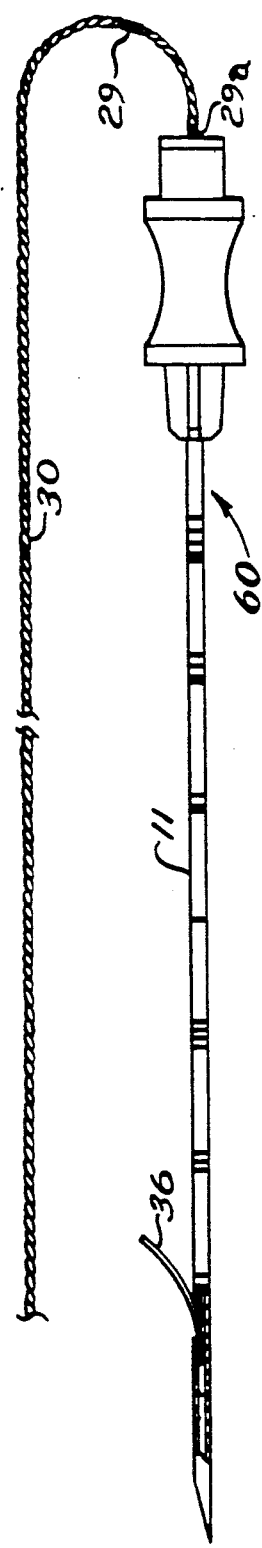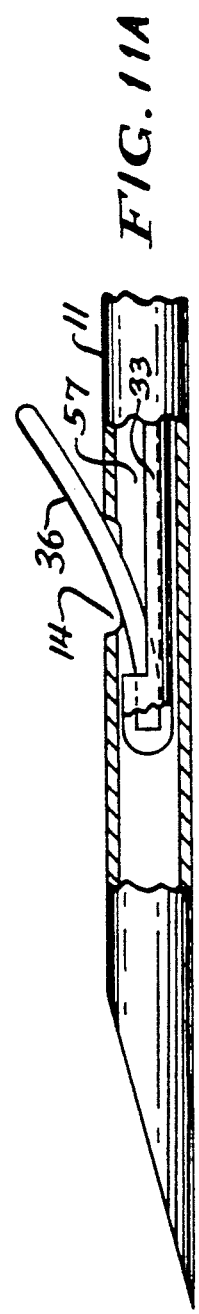

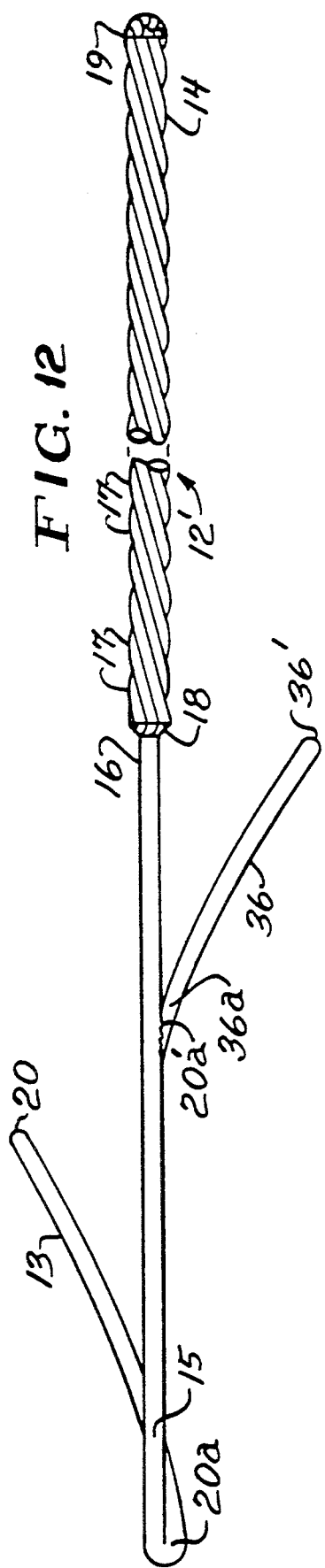
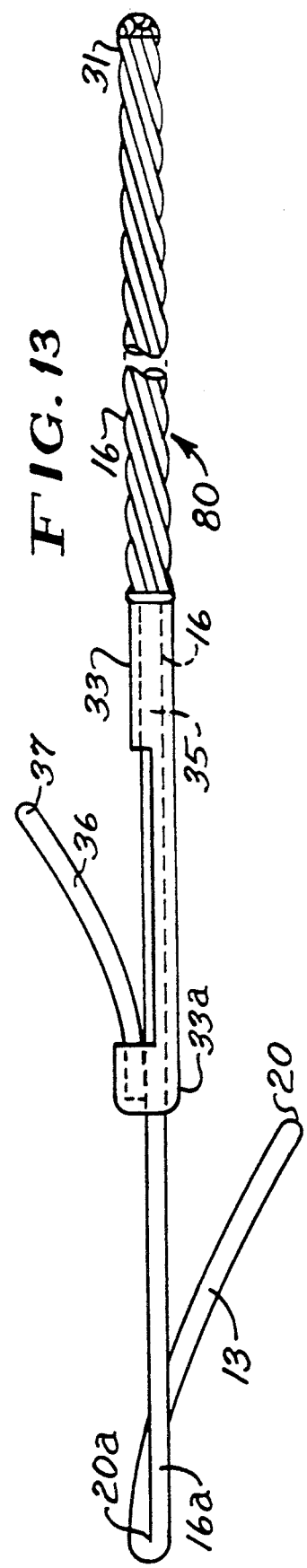
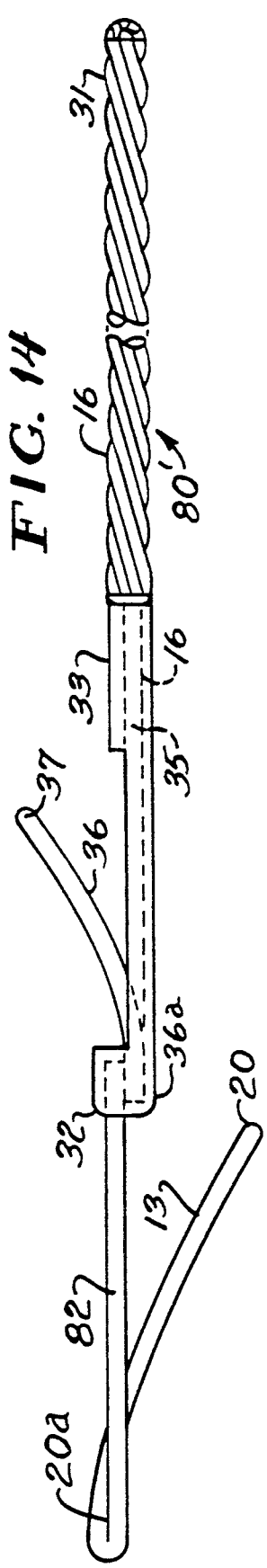

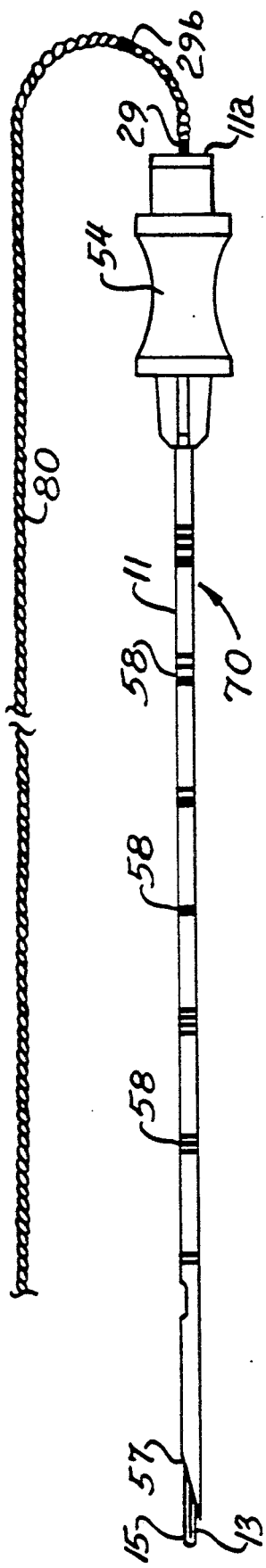
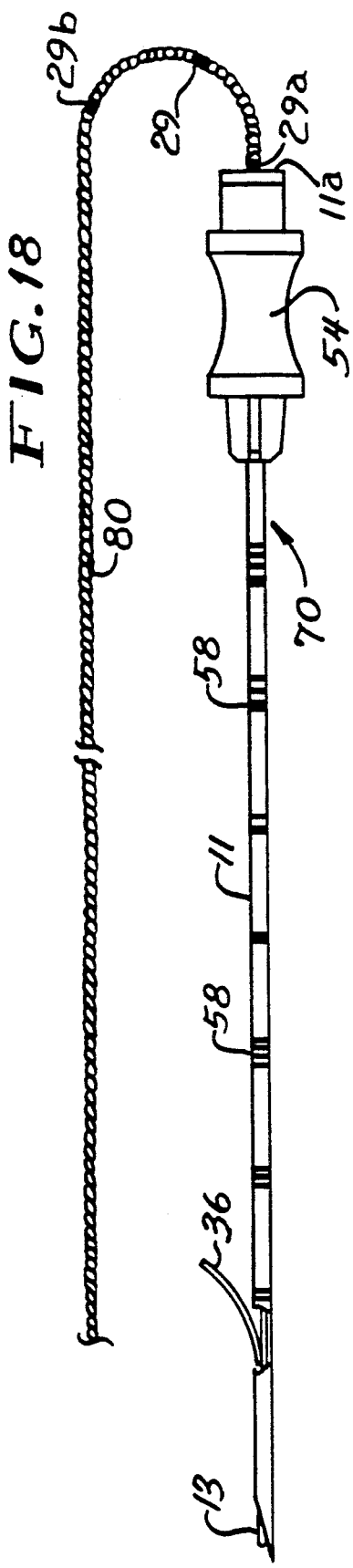

LOCALIZATION NEEDLE ASSEMBLY

BACKGROUND OF THE INVENTION

The present invention relates to a novel localization needle assembly which may be readily inserted into and anchored within body tissue to identify to the surgeon the location of nonpalpable lesions.

Various localization needle systems have been proposed to aid the surgeon in locating nonpalpable lesions within the breast. In one system commonly referred to as a needle and hook-wire system, a hypodermic needle is initially placed into the breast to locate the breast lesion. When the needle is properly placed, a stainless steel wire having a hairpin hooked-end portion is slid through the needle wherein the hooked hairpin-end portion exits from the needle to engage the body tissue to retain the needle adjacent to or at the breast lesion. The introducing needle is withdrawn over the wire and the wire is anchored to the tissue and the patient is taken to surgery. The wire permits the surgeon to locate where the lesion lies within the breast tissue.

However, this needle and wire-hook arrangement possesses several disadvantages. For example, during mammographic filming of the breast lesion and the location of the needle within the breast, the breast is compressed and this can cause the needle to move or be displaced with respect to the breast lesion. Additionally, when the needle and hairpin-end hook wire has been inserted through the needle and expanded to anchor the needle/hook-wire apparatus in place in the fatty tissue within the breast, oftentimes this fatty tissue does not provide sufficient anchoring and/or stability to needle/hook-wire apparatus to permit completion of the medical procedure on the patient. Such migration of the assembly can lead to the failure to adequately complete the removal of non-palpable lesions without undue delay and repositioning procedures.

Another needle/wire device and technique includes a curved-end wire which is made of a tough pseudo-elastic alloy which possesses a memory. A needle containing a wire having a J-shaped hook on the end is inserted into the breast and advanced to identify the location of the breast lesion. The wire is then advanced inwardly such that the curved hooked end engage the body tissue to immobilize the needle during mammography imaging to insure that the needle is correctly positioned at or adjacent the breast lesion. The needle and hook device can be relatively easily displaced if traction or pressure is applied to the breast during transport of the patient or during surgery. Thus, actual migration of the hook-wire device in the fatty tissue of the breast occurs during surgery and movement of the patient to surgery. Such migration of the assembly can lead to the failure to adequately complete the removal of non-palpable lesions without undue delay and repositioning procedures.

Both of those systems employ a single wire needle for anchoring the localization needle assembly to body tissue. The wire needle must be flexible and pliable to allow easy handling and fastening of the proximal end of the wire outside of the patient's body and to resist the risk of unintended penetration or migration. However, because the needle wire must be sufficiently large so as to resist migration and accidental transection by the surgeon during excision, this limits the amount of flexibility and pliability obtainable for known needle anchoring arrangements which employ a single wire.

SUMMARY OF THE INVENTION

It is therefore an object of the present invention to provide a new and improved localization needle assembly for use in locating and pinpointing lesions within a body.

Another object of the present invention is a novel localization needle assembly which may be readily positioned and locked within body tissue to precisely locate an pinpoint lesions for subsequent surgical removal or biopsy.

A further object of the present invention is a novel localization needle assembly which includes a retractable anchoring means located within a cannula, which is adapted to be extended outwardly from the side wall of the cannula to lock and anchor the localization needle assembly to the body tissue, and a fixed anchoring means located at the distal end of the inner cannula to precisely locate lesions within the breast for subsequent surgical removal.

It is yet another object of the present invention to provide a novel localization needle assembly including a needle structure having a rearwardly retractable barb means and a non-retractable barb means for fixedly anchoring the localization needle assembly within the fatty tissue of the breast.

Still another object of the present invention is a needle structure for a localization needle assembly which is characterized by greater flexibility and pliability than that for known comparable sized needles and which resists accidental transection.

These and other objects are achieved by the present invention which provides a localization needle assembly for locating lesions within body tissue, including in combination: an outer tubular cannula member having a distal end and a proximal end with the cannula member having an opening predeterminedly located from the distal end, an elongated inner needle structure having a distal end terminating in a distal tip portion and a proximal end, the needle structure having anchoring means including a first barb located at the distal tip portion and a second barb located proximal of the distal tip portion, the inner needle structure being slidably mounted for movement within the outer cannula member between first and second positions, the second barb being contained within the outer cannula member, extending towards the opening in the outer cannula member when the needle structure is in the first position and the second barb being moved outward of the outer cannula member through the opening predeterminedly located from the distal end of the outer cannula member to engage body tissue when the needle structure is moved to the second position to anchor the localization needle assembly to body tissue, and both of the barbs being deployed to engage body tissue with subsequent movement of the cannula member relative to the inner needle structure in a direction toward the proximal end of the inner needle structure.

With these and further objects of the present invention, the nature of which will become more apparent, the invention will be more fully understood by reference to the drawings, the accompanying detailed description and the appended claims.

The invention consists of certain novel features and structural details hereinafter fully described, illustrated in the accompanying drawings, and particularly pointed in the appended claims, it being understood that various changes in the details may be made without departing from the spirit, or sacrificing any of the advantages of the present invention.

DESCRIPTION OF THE DRAWINGS

For the purpose of facilitating and understanding the invention, there is illustrated in the accompanying drawings a preferred embodiment thereof, from an inspection of which, when considered in connection with the following description, the invention, its construction and operation, and many of its advantages will be readily understood and appreciated.

FIG. 1 is a side view of a localization needle assembly provided by the present invention;

FIG. 2 is an enlarged side view of an inner needle structure of the localization needle assembly shown in FIG. 1;

FIG. 3 is an enlarged side view of a further embodiment of an inner needle structure for a localization needle assembly provided by the present invention;

FIG. 4 is an enlarged side view of another embodiment of an inner needle structure of a localization needle assembly;

FIGS. 5-8 are cross-sectional views for various embodiments of the needle structure illustrated in FIGS. 2 and 3;

FIG. 9 is a side view of an outer cannula of the localization needle assembly shown in FIG. 1;

FIG. 10 is a side view of the localization needle assembly provided by the present invention with the anchoring barb illustrated in its retracted position;

FIG. 10A is an enlarged fragmentary view of the distal end of the localization needle assembly illustrated in FIG. 10; assembly of FIG. 10 but illustrated with the anchoring barb deployed;

FIG. 11A is an enlarged fragmentary view of the distal end of the localization needle assembly of FIG. 11;

FIG. 12 is an enlarged side view of a further embodiment of an inner needle structure for a localization needle provided by the present invention;

FIG. 13 is an enlarged side view of a further embodiment of an inner needle structure of a localization needle assembly provided by the present invention;

FIG. 14 illustrates a modification of the inner needle structure illustrated in FIG. 13;

FIG. 17 is a side view of a localization needle assembly provided by the present invention illustrated with the anchoring barbs in their retracted positions; and FIG. 18 is a side view of the localization needle assembly of FIG. 17 but illustrated with the retractable anchoring barb deployed.

DESCRIPTION OF PREFERRED EMBODIMENTS

Figure 15:
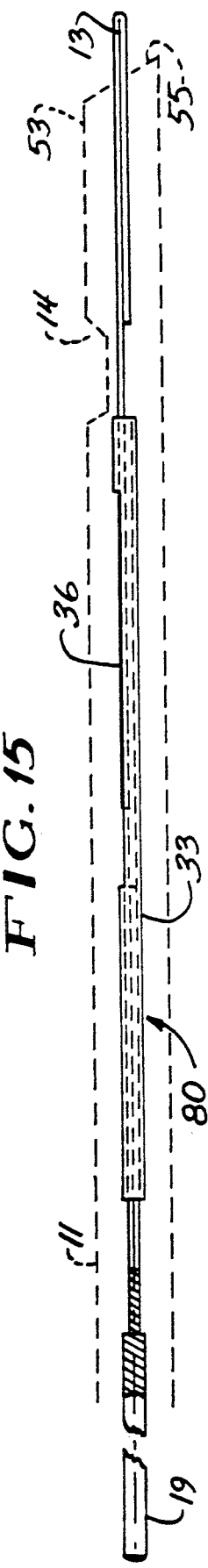
FIG. 15 is a side view of the needle structure with the anchoring barbs illustrated in their retracted positions.

Referring to FIG. 1, there is illustrated a localization needle assembly 10 provided in accordance with the present invention for use in locating lesions within body tissue, and in particular for use as a breast localization needle assembly for locating nonpalpable lesions within the breast. Although the localization needle assembly 10 is specifically described with reference to an application as a breast localization assembly, the localization needle assembly 10 of the present invention has application in locating cancerous nonpalpable lesions within the human or animal body, be it a brain tumor, or any medical procedure which requires the pinpointing of a lesion, foreign body or normal structure within the body or organ of the body.

The localization needle assembly 10 includes a tubular outer cannula 11 and a needle structure 12 which is adapted for sliding movement within the outer cannula 11. The needle structure 12 defines a retractable barb 13, shown deployed in FIG. 1, whereby the barb 13 projects outward through an aperture 14 in the outer cannula 11 for anchoring the localization needle assembly to body tissue as will be described hereinafter. The barb 13 is retracted within the outer cannula 11 during introduction of the needle guide assembly into the patient's body during localization procedures, and is deployed by withdrawing the wire structure by pulling on its proximal end for immobilizing the needle during mammography.

The needle structure 12 has markings 29 and 29a thereon to provide an indication to the user as to the location of the tip and barb relative to the tip and aperture (FIG. 1) of the cannula 11. The markings enable the surgeon to know when the barb is retracted and when it is deployed. For example, marking 29 when aligned with the proximal edge 11a of the cannula indicates that the barb is retracted within the cannula 11. The marking 29a, when aligned with the proximal edge 11a of the cannula 11, indicates that the barb is fully deployed.

Referring to FIG. 2, the needle structure 12 has a proximal end 14' and a distal end 15. The needle structure 12 is formed of an elongated single wire 16 which is reinforced over a portion of its length with multiple wire strands 17 to form a unitary needle wire structure. As illustrated in FIG. 2, for example, the outer wires 17 may be wound (or stranded) in helical fashion around the core wire 16, but terminate short of the distal end of the core wire 16 defining a junction point 18 at which point the outer wires 17 are connected or secured to the core wire 16 in a suitable manner such as by solder or welding. A further solder joint 19 is provided at the tip of the needle structure 11 at the proximal end 14" thereof. These solder connections protect the wire 11 from fraying at the proximal end 14' and at the junction 18.

The distal tip portion of the core wire 16 is bent over on itself and tightened, as is known in the art, to form the barb portion 13 which projects rearwardly from the distal tip, that is, toward the right in FIG. 2, and terminates in a sharp tip or point 20. The overbend may be secured as by solder 20a. The use of reinforcement permits the needle structure 12 to be made of a smaller diameter wire to enhance the flexibility and pliability of the needle structure without compromising its resistance to accidental transection.

For the needle structure 12 illustrated in FIG. 2, the reinforcement is provided by the multiple wire strands 17 which may be wound or stranded on the core wire 16 over a portion of its length. The outer wires 17 may be wrapped on the core wire 16 and/or may be braided before being combined with the core wire. Moreover, although wires of circular cross-section are illustrated, the outer wire or wires could be in the form of a flat band or strip having a rectangular cross-section. Also, although the core wire 16 illustrated in FIG. 2 is a single wire element, the core wire may comprise a two element structure 30 such as that illustrated in FIG. 3 wherein an inner cannula 33 is secured to the distal end of the core wire 16 as will be described. Further, as illustrated in FIG. 4, the reinforcement for a needle structure 40 is provided by coiling the core wire over a portion of its length as will hereinafter be described.

The stranded needle structures 12 and 30 illustrated in FIGS. 2 and 3 may take various forms. Referring to FIG. 5, by way of example, the needle wire structure 12 may comprise a core wire 16 on which may be wound or stranded a plurality of outer wires 17, there being twelve wires 17 illustrated in FIG. 5.

Referring to FIG. 6, in a further embodiment, the needle structure 12a includes twelve outer wires 22 wrapped around six intermediate wires 23 wrapped around a single core wire 16. In FIG. 7, a needle structure 12b includes a single core wire 16 upon which are wrapped six strands 24 each including seven wires 25. In another embodiment for a wire structure 12c shown in FIG. 8, the core 16' comprises a stranded wire including three wires 27 upon which are wound or stranded nine outer wires 28.

The stranded configuration for the needle structure 12 provides reinforcement for the needle structure along substantially its entire length providing many advantages over a conventional wire needle. For example, multiple strands resist accidental transection. Even if several strands were to be cut, functionality of the needle structure would be preserved. Also, strands are more flexible than stiff single wires and the use of strands reduces risk of additional penetration of organs or vessels or migration within cavity due to accidental contact with the needle assembly during normal movement of the patient during diagnostic procedures as during the transportation of the patient to surgery. The flexibility and pliability allow easier handling of the wire structure outside of the patient's body and fastening of the wire structure to the patient's skin with adhesive tape. Moreover, a larger strand has greater tensile strength than a single small diameter wire, and a strand resist fatigue breakage better than does a single wire.

Referring to FIG. 3, there is illustrated a further embodiment for a stranded needle structure 30 having a proximal end 31 and a distal end 32 and which includes a short inner cannula member 33 which is attached to the core wire 16 at its end 35. The needle structure 30 further includes a short wire member 36, the forward end 36a of which is secured to the inner cannula member 33 by soldering, welding, by adhesive or by mechanical means, such as, crimping, threading or shrinking. The short wire member 36 includes a free end 37 defining a barb or hook which is adapted to anchor the needle within body tissue.

Referring to FIG. 4, a further embodiment of a needle structure 40 includes a linear portion 41 at its distal end 42 and a helical portion 43 intermediate its proximal end 44 and its distal end 42, and preferably extending all the way to its proximal end. The needle structure 40 may be formed of a single wire or monofilament which is coiled from the linear portion 41 to its proximal end. The tip of the wire is folded back upon itself to define a rearwardly projecting barb 45.

The helical coiled portion 43 defines the reinforcement for the needle structure 40 while permitting use of a single wire or monofilament. This configuration provides a degree of rigidity of the needle structure in the distal end portion, permitting the barb to anchor the localization needle assembly to body tissue, and with the proximal end portion or helical coiled portion 43 providing flexibility and pliability in the portion of the structure by which the user directs the anchoring distal end to the target.

Referring to FIG. 9, the outer cannula 11 includes a hollow tubular shaft portion 51 having a proximal end 52 and a distal end 53. The cannula may be comprised of a rigid material composed of either steel, polymer or a combination thereof and may be of a variable length as required. A hub 54 is mounted on the proximal end of the shaft 51 to facilitate use of the cannula. The distal end 53 is provided with a sharp point 55. The tubular shaft 51 has an opening 14 formed therethrough at a predetermined distance from the tip 55 of the cannula. Markings 58 are provided on the outer surface of the cannula 11 to provide an indication to the surgeon of the depth to which the cannula has been inserted into the body of the patient being treated.

The use of the needle guide assembly provided by the present invention is described with reference to an embodiment for the needle guide assembly 60 illustrated in FIGS. 10 and 11 which includes the needle structure 30 illustrated in FIG. 3 and the outer cannula 11 illustrated in FIG. 7. However, the needle structures 12 and 40 illustrated in FIGS. 2 and 4, would function in a similar manner in localization procedures.

Referring to FIGS. 10 and 10A, there is illustrated a needle guide assembly 60 which includes the needle structure 30 assembled with the cannula 11. In FIGS. 10 and 10A, the barb 36 is illustrated in the retracted position. In the retracted position, the barb 36 is located within the bore 57 forward of the opening 14 with the barb 36 engaging the inner wall 59 of the tubular shaft 51.

Referring to FIGS. 11 and 11A, the needle guide assembly 60 is illustrated with the barb 36 in the extended position wherein the needle wire structure 30 has withdrawn back into the cannula 11, moving the inner cannula 33 towards the right in FIGS. 11 and 11A, permitting the barb 36 to pass through the opening 14 in the cannula 11 for deployment.

In use, referring to FIGS. 10 and 10A, initially, the needle structure 30 is positioned within cannula 11 so that the tip of the needle structure 30 extends outwardly of the cannula 11 at the distal end 53 of the cannula 11 such that the barb 36 is retracted during insertion of the assembly into the tissue of the body.

The localization needle assembly 60 is advanced to the target area of a human or animal body, either for simply marking the location, be it the breast, liver, ductal structure, brain, lung or other organs where it is desirable to take a biopsy, a sample structure or to surgically remove an unwanted mass or lesion from the body. The desired position is obtained by advancing the needle assembly into the target area using the forward pressure on the hub on the cannula 11 to advance the localization needle assembly 60 into the target. After the needle has been properly positioned using either X-ray, ultrasound, or other imaging means, the inner needle assembly 30 is withdrawn back into the cannula thereby deploying the barb member 36 through opening 14 in the sidewall of the cannula 11 to lock and firmly anchor the localization needle assembly 60 in position within the body tissue, immobilizing the assembly 60. When the localization needle assembly 60 has been inserted into the breast, the movement of the barb member 36 into the body tissue anchors and firmly retains the needle assembly within the breast or body tissue. The opening 14 may be located on the outer cannula at a position where it is desired that the needle assembly be anchored to the body tissue. Preferably this position is adjacent the distal end, but it could be located at any position intermediate the distal and proximal ends provided proper anchoring of the localization needle assembly occurs with respect to the body tissue.

If after deployment of the barb 36, it is determined by X-ray, ultrasound or filming means, that the localization needle assembly has not located a lesion, the barb 36 can be retracted by advancing the stranded needle and the inner cannula attached thereto into the outer cannula 11. The localization needle assembly 60 can then be repositioned to locate the lesion, the inner cannula 33 being moved outwardly of the outer cannula 11 to again deploy the barb 36 when the lesion is located.

As is well known in the art, the length of the outer cannula can vary depending upon the depth of the lesion that is to be localized and identified for subsequent surgical operation.

Referring to FIGS. 12-14, there are illustrated further embodiments for the needle structure 12', 80 and 80' which include dual anchoring means including two barbs. One barb 13 at the distal tip of the needle structure is a fixed barb. The other barb 36, located proximally of the distal tip of the needle structure, is a retractable barb. The retractable barb is adapted to lock and anchor the localization needle assembly to body tissue. The fixed barb is located at the distal tip of the needle structure to precisely locate lesions within body tissue. Needle structure 12' is similar to needle structure 12 illustrated in FIG. 2 and accordingly corresponding elements have been given like reference numerals. Similarly, needle structures 80 and 80' are similar to needle structure 30 illustrated in FIG. 3, and corresponding elements have been given like reference numerals.

Referring to FIG. 12, in needle structure 12', the fixed barb 13 is formed at the distal tip of the core wire 16. The retractable barb 36 projects rearwardly from a point just behind the distal tip and terminates in a sharp tip or point 36'. The barb 36 is attached to the core wire 16 in a suitable manner as by welding or soldering 20a' at its base portion 36a. In FIG. 12, the retractable barb is shown located approximately 180° circumferentially from the fixed barb 13. It has been found that this arrangement minimizes lateral shifting of the needle structure 12' when the same has been positioned and anchored within the body tissue. However, in some applications it may be desirable to have both barbs located along a common axis in the same plane, i.e., aligned along one side of the core wire 16 or have one of the barbs extending in any direction with respect to the other barb to provide enhanced anchoring of the assembly. The needle structure 12'includes a flexible reinforced portion according to any of the embodiments disclosed herein. For example, the reinforced portion may be formed by multiple wires 17 wound as illustrated in FIGS. 5-8, or the flexible reinforced portion may be a helical coiled section of a monofilament. Moreover, in some applications the core wire 16 may not have a reinforced portion. Needle structure 12' is used with the outer cannula 11 as described above.

Referring to FIG. 13, the needle structure 80 is similar to needle structure 30 illustrated in FIG. 3 and includes a short inner cannula member 33 which is attached to the core wire 16 near its distal end 35. In the needle structure 80, the core wire 16 extends through the inner cannula member 33 and has its distal end portion 16a portion extending out through the forward end 33a of the inner cannula member 33 through an opening (not shown). The distal end portion 16a of the core wire 16 is bent over on itself and tightened, as is known in the art, to form the fixed barb portion 13 which projects rearwardly from the distal tip, and terminates in a sharp tip or point 20. The over bend may be secured as by solder 20a. The barb 13 is located 180° circumferentially from the retractable barb 36. Barb 36 comprises a short wire member the forward end 36a of which is secured to the inner cannula member 33 by soldering, welding, by adhesive or mechanical means, such as crimping, threading or shrinking. As for the needle structure 30, the short wire member 36 includes a free end 37 defining a barb or hook which is adapted to anchor the needle within the body tissue as has been described.

Referring to FIG. 14, the needle structure 80' is similar to needle structure 80, but the fixed barb 13 formed at the distal tip of the needle structure 80' comprises a short wire member 82 which is secured to the distal tip of the inner cannula member 33 by soldering, welding, adhesive, or by mechanical means, such as crimping, threading or shrinking. The retractable barb 36 is formed by bending the distal tip of the core wire 16 over on itself or as a separate short wire segment which is secured to the inner cannula 33 in the manner described above for needle structure 30.

Figure 16:
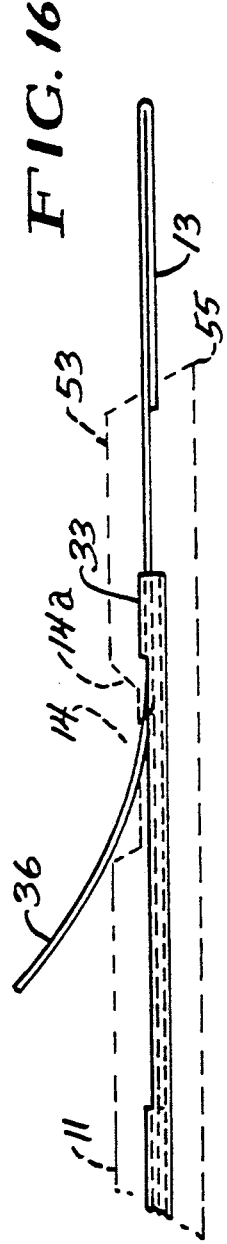
FIG. 16 is a fragmentary view of the needle structure of FIG. 15, but illustrated with the retractable anchoring barb deployed.
Figure 16A:
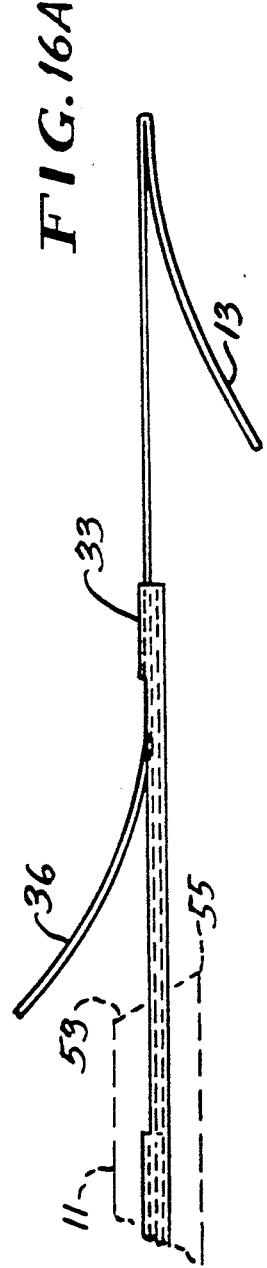
FIG. 16A is a fragmentary view of the needle structure of FIG. 15, but illustrated with both anchoring barbs deployed.

FIGS. 15, 16 and 16A illustrate various positions for the needle structure relative to the outer cannula 11, shown in phantom. FIG. 15 illustrates the needle structure position during positioning of the localization needle assembly, i.e., while a lesion is being targeted. FIG. 16 illustrates the needle positioned to provide a temporary anchoring by the retractable barb 36 during imaging to confirm that a lesion has been precisely located. FIG. 16A illustrates withdrawal of the outer cannula 11 following confirmation of localizing a lesion whereby both barbs are deployed in the body tissue.

Referring to FIG. 15, the needle structure 80 is illustrated in its retracted or undeployed configuration with both the fixed barb 13 and the retractable barb 36 extending generally axially of the core wire 16 and lying along the core wire 16. The needle structure 80 is illustrated positioned within the cannula 11, shown in phantom, with a portion of the fixed barb 13 extending slightly beyond and out of the distal end 53 of the cannula 11 and with the retractable barb 3 and the inner cannula 33 located rearwardly of the opening 14 in the cannula 11.

Referring now to FIG. 16, which is a fragmentary view similar to FIG. 15, the needle structure 80 is shown with the retractable barb 36 in its deployed or extended condition. The fixed barb 13 is maintained in its "folded" or retracted condition by its engagement with the distal end 53 of the outer cannula. In this position, the inner cannula 33 distal end is located forwardly past the opening 14.

Referring to FIG. 16A, the outer cannula 11 is shown withdrawn past the two barbs 13 and 36. Initially, as the outer cannula is withdrawn from the position shown in FIG. 16, the tip of barb 13 is released from within the distal end of the cannula 11 and the barb 13 flexes outwardly to its deployed position. With continued withdrawing movement of the cannula 11 toward the left in FIGS. 16 and 16A, the retractable barb 36 initially is engaged by the cannula 11, and particularly the forward edge 14a of opening 14, causing the barb 36 to be retracted into the cannula 11. When the distal end of the cannula 11 is moved past the barb 36 to the position shown in FIG. 16A, and the barb 36 is out of engagement with the cannula, barb 36 flexes outwardly to its deployed position in the body tissue to anchor the assembly.

Referring to FIGS. 17 and 18, needle guide assembly 80 is illustrated assembled with the cannula 11. In FIG. 17, both the fixed barb 13 and retractable barb 36 are illustrated in the retracted position. When in the retracted position, the retractable barb 36 is located within the bore 57 forward of the opening 14 with the barb 36 engaging the inner wall of the cannula 11. In FIG. 18, the needle guide assembly 80 is illustrated with the barb 36 in the extended position after the needle wire structure 80 has withdrawn slightly back into the cannula 11, moving the inner cannula 33 towards the right in FIG. 18, permitting the barb 36 to pas through opening 14 in cannula 11 for deployment. The fixed barb 13 is maintained folded over, or nondeployed, by the distal end of the cannula 11.

In use, referring to FIGS. 17 and 18, initially, the needle structure 80 is positioned within cannula 11 so that the tip of the needle structure 80, including a portion of folded fixed barb 13 extends outwardly of the cannula 11 at the distal end 53 of the cannula 11 and the retractable barb 36 is retracted within cannula 11. This relative positioning of the needle structure 80 and the cannula 11 is maintained during insertion of the assembly into the body. The fixed barb 13 is maintained in its folded position by the forward distal tip of the cannula 11. Markings 58 are provided on the outer surface of cannula 11 to provide an indication to the surgeon of the depth to which the cannula has been inserted into the body of the patient being treated The manner in which the localization needle assembly 80 is advanced to a target area within a human or animal body has been described hereinabove.

Referring to FIG. 18, when the tip of the needle assembly 70 reaches the target area, and a lesion is located, the retractable barb 36 is deployed to anchor the distal end of the needle assembly while desired positioning is confirmed. Markings 29, 29a and 29b on the needle structure 80 indicate the position where both barbs are contained within the outer cannula 11, the position where the retractable barb 36 is deployed through opening 14 and the position where both barbs are deployed external to the cannula, respectively. Retractable barb 36 is indicated as being retracted when marking 29 is adjacent to the proximal end 11a of the handle (FIG. 17) and the barb 36 is deployed when the wire structure 80 is withdrawn slightly from the cannula 11 until marking 29a is located at the proximal end 11a of the handle (FIG. 18).

When the positioning is satisfied with precise targeting of the lesion, the outer needle 11 is removed, leaving the double barb in place with both barbs 13 and 36 deployed and localizing the lesion to be removed for biopsy procedure.

The fixed barb 13 defines a fixed anchoring means for the needle structure 80 and the retractable barb 36 defines a temporary anchoring means for the needle structure. Thus, when the needle structure is in place in fatty tissue within the breast, and the fatty tissue does not provide sufficient anchoring and/or stability to the distally located fixed barb 13, the retractable barb 36 supplements the anchoring afforded by barb 13 to provide the requisite stability to the needle structure to permit completion of the medical procedure on the patient and substantially prevents migration of the needle structure.

Although only a single fixed barb 13 has been illustrated in the drawings, it is within the scope of the present invention that a fixed barb may be comprised of a plurality of barbs or tissue anchoring elements.

We claim:

1. A localization needle assembly for locating lesions within body tissue, including in combination: an outer tubular cannula member having a distal end and a proximal end with said cannula member having an opening predeterminedly located from said distal end, an elongated inner needle structure having a distal end terminating in a distal tip portion and a proximal end, said needle structure having anchoring means including a first barb located at the distal tip portion and a second barb located proximal of said distal tip portion, said inner needle structure being slidably mounted for movement within said outer cannula member between first and second positions, said second barb being contained within said outer cannula member, extending towards said opening in said outer cannula member when said needle structure is in said first position and said second barb being moved outward of said outer cannula member through said opening predeterminedly located from the distal end of said outer cannula member to engage body tissue when said needle structure is moved to said second position to anchor the localization needle assembly to body tissue, and both of said barbs being deployed to engage body tissue with subsequent movement of said cannula member relative to said inner needle structure in a direction toward the proximal end of said inner needle structure.

2. A localization needle assembly according to claim 1, wherein said anchoring means further comprises a hollow generally cylindrical inner cannula secured to said distal end of said needle structure and adapted to be received within said outer cannula member for sliding movement therewithin, said second barb comprising a segment of wire having a fixed end secured to said inner cannula and a free end projecting rearwardly of the distal end of said outer cannula member.

3. A localization needle assembly according to claim 1, wherein the distal tip portion of said needle structure is folded over upon itself with its tip portion projecting rearwardly defining said first barb.

4. A localization needle assembly according to claim 1, wherein said first and second barbs are spaced apart circumferentially approximately 180°.

5. A localization needle assembly for locating lesions within body tissue, including in combination: an outer tubular cannula member having a distal end and a proximal end with said cannula member having an opening predeterminedly located from said distal end, an elongated inner needle structure having a distal end having a distal tip and a proximal end, with a linear portion at its distal end and a flexible reinforced portion intermediate its proximal and distal ends, said linear portion of said needle structure having anchoring means including a first barb and a second barb, said first barb being located at the distal tip of said needle structure and said second barb being located proximal of said distal tip, said inner needle structure being slidably mounted for movement within said outer cannula member between first and second positions, said second barb being contained within said outer cannula member, extending towards said opening in said outer cannula member when said needle structure is in said first position and said second barb being moved outward of said outer cannula member through said opening predeterminedly located from the distal end of said outer cannula member to engage body tissue when said needle structure is moved to said second position to anchor the localization needle assembly to body tissue, and both of said barbs being deployed to engage body tissue with subsequent movement of said cannula member relative to said inner needle structure in a direction toward the proximal end of said inner needle structure.

6. A localization needle assembly according to claim 5, wherein said anchoring means further comprises a hollow generally cylindrical inner cannula secured to said distal end of said needle structure and adapted to be received within said outer cannula member for sliding movement therewithin, said second barb comprising a segment of wire having a fixed end secured to said inner cannula and a free end projecting rearwardly of the distal end of said outer cannula member.

7. A localization needle assembly according to claim 5 wherein the distal end of said linear portion of said needle structure extends through said inner cannula axially thereof with its distal tip portion located beyond the distal end of said inner cannula, and said distal tip portion of said needle structure being folded over upon itself with its tip portion projecting rearwardly, defining said first barb.

8. A needle assembly comprising: an elongated single wire needle reinforced over a portion of its length with multiple wire strands to form a unitary wire needle structure having a distal end portion and a proximal end portion, said needle structure having anchoring means including a first barb means positioned at said distal end portion adapted to engage body tissue to anchor the needle structure to body tissue and a second barb means located proximal of said distal end portion, and an outer cannula member having an opening predeterminedly located from the distal end of said outer cannula member, with said second barb means cooperating with said opening predeterminedly located from the distal end of said outer cannula member to extend therethrough to anchor the needle to the body tissue.

9. A surgical needle comprising: an elongated wire having a proximal end and a distal end and anchoring means including a first fixed barb means positioned at said distal end and adapted to engage body tissue to anchor the needle to body tissue and a second retractable barb means located proximal of said distal end and adapted to engage body tissue.

10. A surgical needle according to claim 9, wherein said anchoring means further comprises a hollow generally cylindrical inner cannula secured to said distal end of said wire.

11. A surgical needle according to claim 10 wherein the distal end of said wire extends through said inner cannula axially thereof with its distal tip portion located beyond the distal end of said inner cannula, and said distal tip portion of said wire being folded over upon itself with its tip portion projecting rearwardly, defining said first barb.

12. A surgical needle according to claim 10 wherein said second barb means comprises a segment of wire having a fixed end secured to said inner cannula and a free end projecting outwardly from said inner cannula.

13. A surgical needle according to claim 9 wherein said wire has a distal tip folded over upon itself with a portion thereof projecting rearwardly defining said first barb means.

14. A surgical needle comprising: an elongated needle structure having a distal end and a proximal end, with a linear portion at its distal end and a reinforced portion intermediate its proximal and distal ends, said linear portion of said needle structure having anchoring means including a first fixed barb means positioned at said distal end and adapted to engage body tissue to anchor the needle structure to body tissue and a second retractable barb means located proximal of said distal end.

15. A surgical needle according to claim 14, wherein said anchoring means comprises a hollow generally cylindrical inner cannula secured to said linear portion of said needle structure, and wherein said second barb means comprises a segment of wire having a fixed end secured to said inner cannula and a free end projecting outwardly from said inner cannula.

16. A surgical needle according to claim 14, wherein the tip of said linear portion is folded over upon itself with its tip portion projecting rearwardly defining said first barb means.

17. A surgical needle according to claim 14, wherein a plurality of wires are helically wound together to provide said reinforced portion.

* * * * *